United States Patent [19]

Munsch

[11] 4,386,622
[45] Jun. 7, 1983

[54] BREAKAWAY VALVE

[75] Inventor: John M. Munsch, Libertyville, Ill.

[73] Assignee: Baxter Travenol Laboratories, Inc., Deerfield, Ill.

[21] Appl. No.: 282,507

[22] Filed: Jul. 13, 1981

Related U.S. Application Data

[62] Division of Ser. No. 86,102, Oct. 18, 1979, Pat. No. 4,340,049.

[51] Int. Cl.³ .............................................. A61M 5/00
[52] U.S. Cl. .................................. 137/1; 137/68 R; 251/342; 604/244; 604/408
[58] Field of Search ............ 128/214 R, 214.2, 214 C, 128/214 D, 247, 272.3, 274; 137/68 R, 797; 251/342; 137/1

[56] References Cited

U.S. PATENT DOCUMENTS

| | | |
|---|---|---|
| 1,327,190 | 1/1920 | Biginey . |
| 1,913,116 | 6/1933 | Hambaugh ............ 137/533.17 |
| 2,073,941 | 3/1937 | Lower .................... 220/48 |
| 2,499,150 | 2/1950 | Lofl ...................... 130/8 |
| 2,571,144 | 10/1951 | Lofl ...................... 150/8 |
| 2,893,611 | 7/1959 | Akers .................... 222/536 |
| 2,894,510 | 11/1964 | Benson ................... 137/68 R |
| 3,205,889 | 9/1965 | Alder .................... 128/272 |
| 3,217,710 | 11/1965 | Beall et al. .............. 128/214 |
| 3,470,893 | 10/1969 | Nelson ................... 137/68 R |
| 3,482,572 | 12/1969 | Grosllaude ............... 128/214 C |
| 3,509,879 | 5/1970 | Bathish .................. 128/214 |
| 3,545,671 | 12/1970 | Ross ..................... 233/26 |
| 3,788,374 | 1/1974 | Saijo .................... 150/1 |
| 3,858,739 | 1/1975 | Turner ................... 215/32 |
| 3,905,368 | 9/1975 | Lewis .................... 128/272 |
| 3,913,207 | 10/1975 | Freg ..................... 29/413 |
| 3,980,224 | 9/1976 | Yasuda ................... 229/51 |
| 3,994,412 | 11/1976 | Difiglio ................. 220/266 |
| 4,007,738 | 2/1977 | Yoshimo .................. 128/214 D |
| 4,181,140 | 1/1980 | Bayham ................... 251/342 X |
| 4,195,632 | 4/1980 | Parker ................... 128/214 D |

FOREIGN PATENT DOCUMENTS

| | | |
|---|---|---|
| 1129284 | 1/1957 | France . |
| 2028124 | 3/1972 | France . |
| 2098873 | 10/1972 | France ........... 128/214 R |
| 49-10156 | 3/1974 | Japan . |
| 773342 | 4/1957 | United Kingdom . |
| 1460841 | 1/1977 | United Kingdom . |
| 1522798 | 8/1978 | United Kingdom . |
| 2002869 | 2/1979 | United Kingdom . |

Primary Examiner—Alan Cohan
Attorney, Agent, or Firm—Paul C. Flattery; Garrettson Ellis

[57] ABSTRACT

A frangible or breakaway valve for use in a flexible tube. The valve comprises two parts: a tubular portion with a closed end and an elongated, generally rigid handle breakably attached to the closed end. The elongated handle has projections which frictionally contact the interior surface of the flexible tube and prevent the elongated handle from moving back into a closed position once the elongated handle has been broken. The valve may be used in conjunction with tubing and a plastic container of dialysis solution. The valve is opened by breaking away the elongated, generally rigid handle and moving "walking" the rigid handle down the tube by folding the tube back and forth upon itself. The projections on the rigid breakaway handle have sufficient frictional contact with the inside of the tube to assure that the handle will not move back into contact with the tubular portion, and the valve will remain open.

4 Claims, 8 Drawing Figures

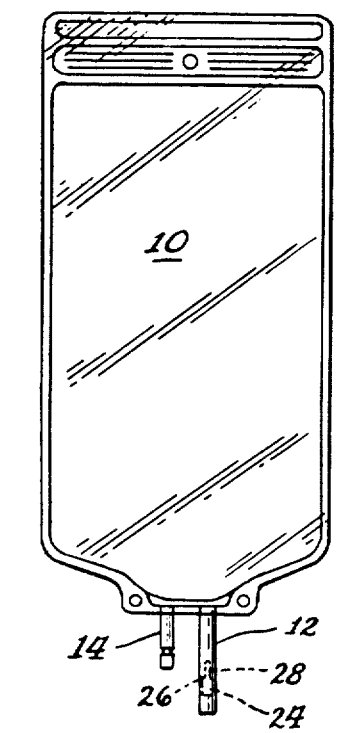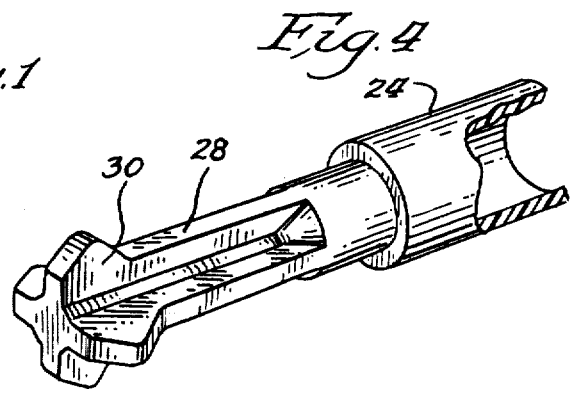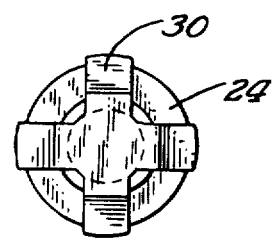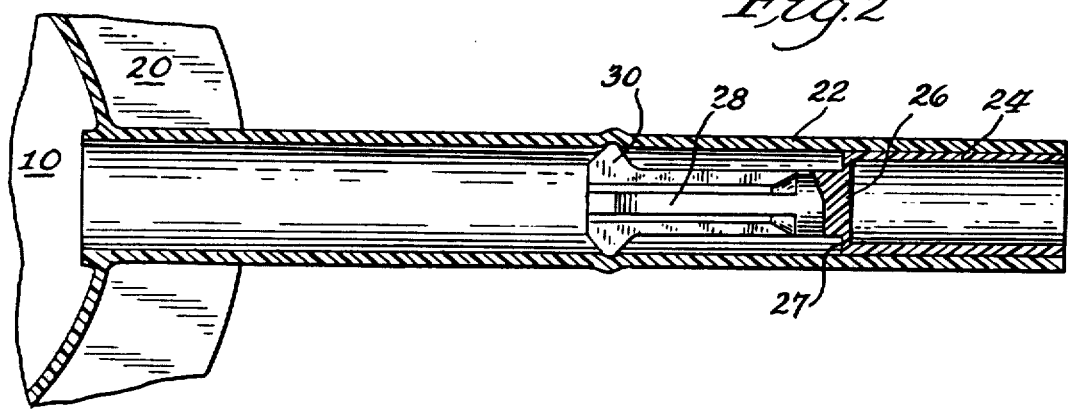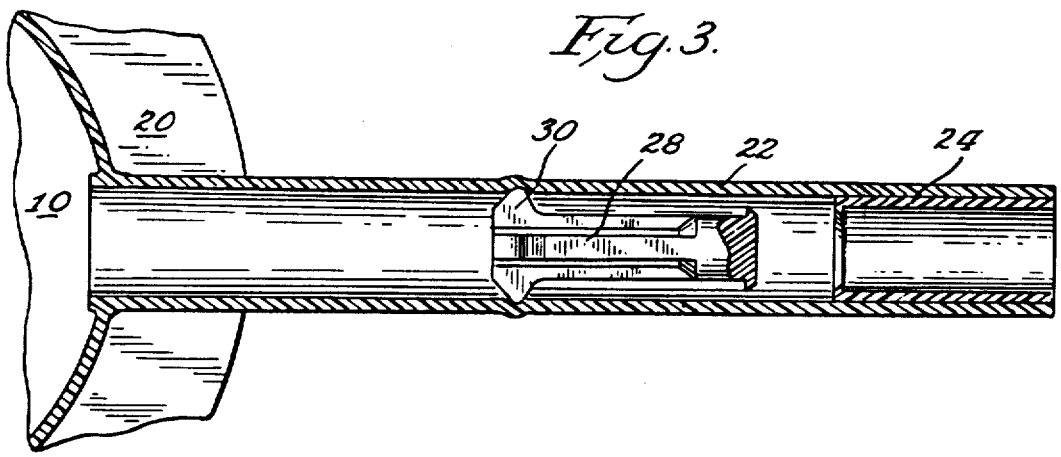

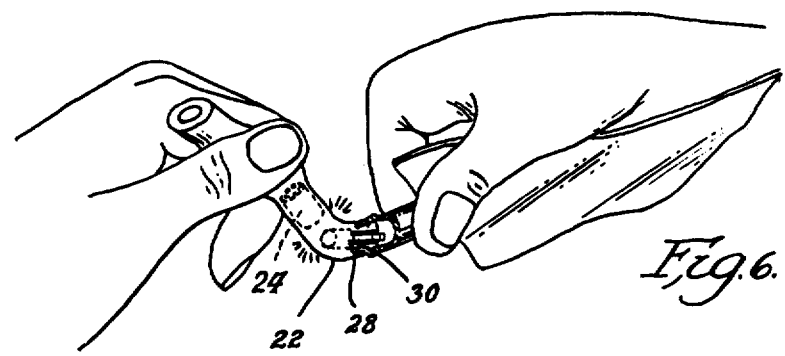
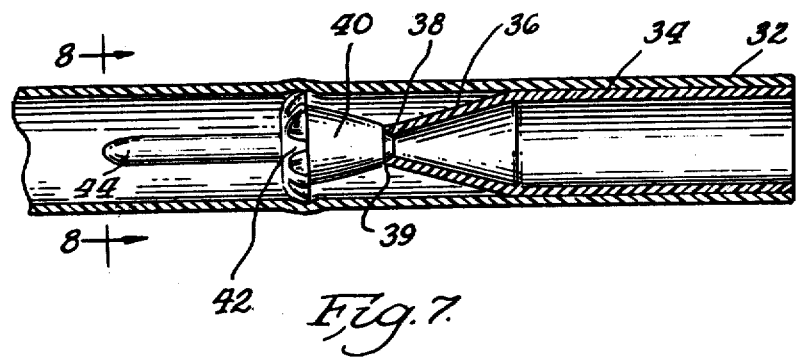
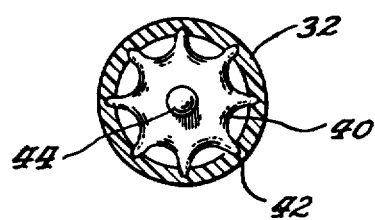

BREAKAWAY VALVE

CROSS-REFERENCE TO RELATED APPLICATION

This application is a division of U.S. application Ser. No. 86,102, filed Oct. 18, 1979 now U.S. Pat. No. 4,340,049 issued July 20, 1982.

BACKGROUND OF THE INVENTION

This invention relates to an improved frangible or breakaway valve in a flexible circular tube, principally for use in conjunction with a peritoneal dialysis solution container or blood bag.

Currently, the most widely used method of kidney dialysis for treatment of End Stage Renal Disease (ESRD) is "hemodialysis." Here, the patient's blood is cleansed by passing it through an artificial kidney in an artificial kidney dialysis machine. By the process of diffusion across a semipermeable membrane in the artificial kidney, impurities and toxins are removed from the patient's blood to thereby perform a function of the patient's natural kidneys. Hemodialysis is required several times a week, each dialysis requiring several hours in a dialysis center or at home. During dialysis, the patient is "tied" to the machine by venous and arterial blood lines which convey his blood to and from the artificial kidney.

Although used less frequently than hemodialysis, a procedure known as "intermittent peritoneal dialysis" is an accepted method for treating ESRD. In this procedure, a dialysis solution is infused into the patient's peritoneal cavity by means of tubing and a catheter. The peritoneum, which defines the peritoneal cavity, contains many small blood vessels and capillary beds which acts as a natural semipermeable membrane. This natural membrane may be contrasted with the artificial membrane used in hemodialysis. In both cases, however, impurities and toxins in the blood are removed by diffusion across a membrane—a cellulose membrane of an artificial kidney or a peritoneal membrane of a peritoneal cavity.

In intermittent peritoneal dialysis, dialysis solution remains in the patient's peritoneal cavity for a time sufficient for blood impurities to be removed by diffusion across the peritoneal membrane into the dialysis solution. The impurity containing dialysis solution then is drained from the peritoneal cavity by means of the catheter and tubing, and a fresh supply of dialysis solution is infused. Intermittent peritoneal dialysis utilizes pumps or other auxiliary equipment to which the patient is "tied" during dialysis; here also the patient must remain sedentary.

Continuous ambulatory peritoneal dialysis is another type of peritoneal dialysis which uses the peritoneum as a semipermeable membrane. This procedure has the important advantage, however, of enabling the patient to be ambulatory and conduct a normal routine during dialysis. The patient is not "tied" to a machine and he must be sedentary only for the time period required to drain and infuse dialysis solution from and into the peritoneal cavity. This infusion and draining is handled by tubing and a surgically implanted, indwelling catheter in the patient's abdominal wall and in communication with his peritoneal cavity.

The continuous ambulatory peritoneal dialysis procedure is intended to be a patient self-care technique once the catheter is surgically implanted. Thus, it is important that the apparatus involved, e.g., tubing and solution container, be simple and easy to use. The present invention is intended to simplify the procedure for infusing dialysis solution into the peritoneal cavity. The invention concerns a novel breakaway valve in the tubing which is attached to or may be a part of the peritoneal dialysis solution container.

Breakaway valves in flexible tubes for use in blood bags are known in the art. The prior art valves typically consist of two parts: a hollow tubular portion bonded to the interior of a flexible tube and a rigid breakaway portion or handle integral with the hollow tubular portion. The handle is breakable by manual manipulation. After breaking, it moves away from its interface with the tubular portion and fluid can flow past it and through the tubing.

An example of a frangible valve in a blood bag is shown in Yoshino U.S. Pat. No. 4,007,738. Here the valve is opened by manually breaking a reduced annular section to effect fluid flow within the blood bag tubing, the breakaway portion floating freely within the tube. Another frangible valve used in a blood bag is shown in French Pat. No. 2,098,873. Here the breakaway portion falls into the blood bag. In U.S. Pat. No. 4,181,140 of Edward L. Bayham, et al.; U.S. Pat. No. 4,294,247 issued Oct. 13, 1981 of Carter, et al., filed Feb. 26, 1979; and U.S. Pat. No. 4,270,534 issued June 2, 1981, all owned by the assignee of this application, frangible valves for flexible tubes in conjunction with blood bags are disclosed. These three patents show frangible valves of various embodiments, some with locking hold-open means. In all prior art breakaway valves, fluid flow is in one direction only. The force of the fluid flow tends to push the broken away part of the valve away from the opening. In practicing the continuous ambulatory peritoneal dialysis procedure fluid flow will be in two directions —one direction during infusion, and the opposite direction during drain.

Some disadvantages of the known frangible valves include: (1) the inability to assure that the breakaway portion will remain in an open position after being broken, (2) the complex configuration required to lock the breakaway portion in a hold-open position, and (3) the difficulty in manually breaking the valve and moving it to an open position. The latter disadvantage is particularly significant when a person does not have good manual dexterity or strength.

Thus, there is a need to provide a frangible valve in a flexible tube which can be easily broken and moved to and remain in an open position. A valve configuration which is simple in design is also desirable for ease of molding and manufacture.

With the advent of dialysis solutions contained in plastic bags, and the development of continuous ambulatory peritoneal dialysis, a simple frangible valve for use by patients in establishing flow from a peritoneal dialysis solution bag via tubing and a catheter to the patient's peritoneal cavity is desired. A simple effective frangible valve which after breaking will remain locked in a hold-open position would, in addition to its potential use in blood bags, be important, particularly from a patient self-care standpoint, when practicing continuous ambulatory peritoneal dialysis. It is, therefore, an object of this invention to provide an improved frangible valve in a flexible tube which has a simple, effective hold-open feature for use in peritoneal dialysis solution bags for continuous ambulatory peritoneal dialysis patients, is easy to open, and easy to move to a hold-open position.

Breaking of the valve of this invention is done by bending the exterior of the flexible, circular tubing back upon itself at the point where the handle joins the closed end of the tubular portion. The initial bending action, and subsequent bending, will "walk" the handle down the tube and away from the now opened tubular portion. Ease of breaking is important for the practice of continuous ambulatory peritoneal dialysis because of the large number of patients with limited physical capacity because of poor eyesight, weakness, arthritis and the like. This invention also is particularly advantageous for use by children and geriatric patients for these same reasons.

The valve of this invention remains in a hold-open position because of projections on the handle. They frictionally contact the interior of the flexible tube; they tightly grip or "bite" into the soft, flexible tubing. Some of the known breakaway valves used in blood bags have provided for frictional contact at a special reduced conical section in the tube. The valve of this invention eliminates the need for any special insert or section (conical, or otherwise) in the tube to hold the broken away handle. The size of the flexible, circular tubing can remain constant, unlike existing blood bag valves with hold-open means in which the valve is locked into a conical section of tubing of reduced cross section.

SUMMARY OF THE INVENTION

The frangible valve of the present invention comprises two integral parts: an elongated, generally rigid handle and a tubular portion with a closed end integral with the handle. The elongated handle carries outwardly extending projections for frictional contact with the interior surface of a flexible circular tube. A frangible zone of weakness is located at the junction of the tubular portion and the elongated handle. When broken by exterior manipulation, the handle moves away from the tubular portion and takes a portion of the closed end with it, thereby permitting flow in the tube.

The frangible zone of weakness may be an annular line of tearing weakness, or may result from the geometry of the tubular portion and handle without need for a specially formed line of tearing weakness. The preferred valve is breakable by exterior manual manipulation, accomplished by bending the flexible tube back upon itself causing the rigid breakaway handle to "walk" down the flexible tube away from the valve opening.

As the rigid handle is broken away in the tube, the handle is "walked" down in frictional contact with the interior surface of the tube. This allows the valve to remain in an open position and permits uninterrupted fluid flow as the projections on the handle "bite" into the tube and prevent the handle from moving back toward the previously closed end. The position of the handle remains fixed regardless of the direction of fluid flow through the valve in the tube. The frictional contact is sufficient to prevent the valve from accidentally closing because of the "biting" action of the projections on the handle. The frictional fit of the projections within the flexible tube is a simple means of assuring that the valve remains open, this simplicity distinguishing it from prior valves which lock in an open position by means of a locking configuration difficult to fabricate and which because of their design can only be assured to permit uninterrupted flow in one direction.

BRIEF DESCRIPTION OF THE DRAWINGS

Other objects, features and advantages of the present invention will become more fully apparent from the following detailed description of the preferred embodiment, the appended claims and the accompanying drawings in which:

FIG. 1 is a view of a solution container for using the valve of the present invention in the outlet port of the container;

FIG. 2 is a greatly enlarged view of the preferred embodiment of the valve of this invention, in conjunction with the solution container of FIG. 1, with some of the parts shown in longitudinal section;

FIG. 3 shows the valve in the open position;

FIG. 4 is a perspective view, with portions broken away, of the valve of this invention;

FIG. 5 is an end view of the valve of this invention viewed from the elongated, generally rigid handle to the tubular portion;

FIG. 6 is a fragmentary, perspective view showing a tube integral with a solution container, a portion of the tube shown in cross section, the valve of this invention in the tube shown being opened by manual exterior manipulation;

FIG. 7 is a view of an alternative embodiment of the valve of this invention in a flexible tube, with some of the parts shown in longitudinal section; and FIG. 8 is an end view of the embodiment of FIG. 7 showing the elongated, generally rigid handle in frictional contact with the interior of a flexible tube.

DETAILED DESCRIPTION OF THE PREFERRED EMBODIMENT

The preferred embodiment of the valve of this invention is illustrated by way of example in FIGS. 2-5. FIG. 1 shows the valve in a preferred embodiment, that is, the outlet port of a peritoneal dialysis solution container. The valve may be positioned, however, anywhere within the tubing connecting the dialysis solution container to the catheter implanted in the patient.

Referring to FIG. 1, a peritoneal dialysis solution container 10 is shown with a tubular outlet port 12 and a tubular medication injection port 14; both ports are in communication with the inside of the solution container 10. The frangible valve of the invention is shown interiorly fitted in port 12. It has a tubular portion 24 and an elongated, generally rigid handle 28 extending from and integral with the closed end 26 of tubular portion 24. Tubular portion 24 is sealed into outlet port 12 by means of a solvent bonding, heat bonding or other bonding techniques known in the art.

Referring to FIGS. 2-5, the valve is shown by way of example with a peritoneal dialysis solution container 10 which has a flat seal 20 which seals a flexible circular tube 22 (port 12 of FIG. 1) in communication with the interior of container 10.

Sealed within the distal end of flexible tube 22 is a tubular portion 24, having a closed end 26. Closed end 26 has extending from and integral with it an elongated, generally rigid handle 28. Closed end 26 has an annular zone of weakness 27 to facilitate breaking the handle 28 from tubular portion 24 thereby opening the valve. Tubular portion 24 and handle 28, which form the valve, are preferably a molded, chemically inert, rigid plastic. The plastic of the preferred embodiment is polyvinyl chloride.

Handle 28 includes a plurality of outwardly extending projections 30 which frictionally fit within the interior of flexible tube 22. Projections 30 dig into the interior of tube 22 and hold the handle 28 in position after it is broken away from closed end 26. This assures that fluid can flow in two directions, one way for infusion of dialysis solution and the opposite way for drainage, without the handle moving back into contact with the closed end 26 and blocking flow. The frictional fit of the handle projections 30 in the walls of tube 22 distinguish the valve of this invention from prior art valves.

The valve of the present invention may be opened manually by manipulating flexible tube 22 at the valve's annular zone of weakness 27. By bending flexible tube 22 back upon itself at the valve's annular zone of weakness 27, handle 28 is broken away from tubular portion 24 and takes a portion of closed end 26 with it. Continued bending moves handle 28 toward the proximal end of tube 22, in effect, "walking" it toward solution container 10. The frictional projections 30 are spaced from each other to avoid adversely affecting fluid flow within the flexible tube.

The valve could also be oriented in the tube 22 such that the handle would be walked away from, rather than toward, the container 10.

Referring to FIG. 6, a partial perspective view is shown with tube 22 shown in partial cross section. Hands are shown bending the tube 22 to break handle 28 from the valve. Tubular portion 24 of the valve remains in place within flexible tube 22 since it is bonded to the interior of flexible tube 22. Outwardly extending projections 30 of rigid handle 28 maintain frictional contact with the interior of flexible tube 22 as the valve is opened and the rigid handle is "walked" down the tube by manual bending and releasing of flexible tube 22. The force created by folding the tubing back upon itself "walks" handle 28 down tube 22 where it remains after the force is released. Handle 28 can be "walked" further down tube 22 by again folding tube 22 back upon itself and releasing. Projections 30 assure that the handle 28 will remain away from the valve opening by frictionally "biting" into the flexible tube 22.

Referring to FIGS. 7 and 8, an alternative embodiment of the invention is shown bonded within a flexible tube 32. The valve has a tubular portion 34 with a conical section 36 thereof of reduced cross section and closed end 38. An elongated, generally rigid handle 40 extends from closed end 38. It has a plurality of projections 42 which frictionally contact the interior of tube 32. The closed end 38 has an annular zone of weakness 39 to aid in opening the valve. Extending parallel to the longitudinal axis of handle 40 from the portion of the handle carrying projections 42 is a generally rigid, elongated member 44 which aids in tearing away at the zone of weakness 39 by giving leverage to the patient to break the valve open. It is easier for weak or elderly patients to open this embodiment of the valve because of the mechanical advantage gained by the member 44 and annular zone of weakness 39. The tubing 32, as in the previously described embodiment, is bent back upon itself to cause generally rigid, elongated handle 40 to "walk" toward the proximal end of tube 32.

The present invention provides an improved valve in a flexible tube which can be easily manually manipulated for the purpose of opening the valve to allow flow through the tube. The valve remains in the open position by means of projections on the rigid handle of the valve "biting" into the flexible tube. In addition, because of the design of the valve, a simple method can be used to effect its opening by bending at the junction of the handle and the closed end of the tubular portion. The tube is bent back upon itself to cause the generally rigid handle of the valve to move or "walk" away from the tubular portion of the valve. Thus, the valve of the present invention has an important advantage of simplicity in design in using frictional contact to remain open. It also has the advantage of a simplified patient method for opening and assuring the continued open position of the valve.

While the present invention has been disclosed in connection with the preferred embodiment thereof and an alternative embodiment thereof, it should be understood that there may be other embodiments, which fall within the sphere and scope of the invention as defined by the following claims.

What is claimed is:

1. The method of opening a valve inside a flexible tube, said valve comprising a tubular portion having a closed end to prevent fluid flow in the tube, a handle extending from and integral with the closed end of the tubular portion, a zone of weakness positioned whereby at least a portion of the closed end is removable by manipulating the handle to separate said closed end from the tubular portion to permit fluid flow through the valve, and projection means extending radially outwardly from the handle and pressing in frictionally retaining relation with the interior surface of the flexible tube, which method comprises:

bending said handle and flexible tube about the handle to sever said zone of weakness, and continuing said bending of the flexible tube to cause the handle and closed end to "walk" along the flexible tube away from the remainder of said valve.

2. The method of claim 1 in which one repeatedly bends said flexible tube to cause said handle and closed end to "walk" along the tube.

3. The method of claim 2 in which said zone of weakness is at the junction of said handle and closed end.

4. The method of claim 1 in which said tube is repeatedly folded back upon itself to "walk" said handle and closed end down the tube.

* * * * *